United States Patent [19]
Dwork

[11] Patent Number: 5,522,380
[45] Date of Patent: Jun. 4, 1996

[54] METERED DOSE MEDICATION ADAPTOR WITH IMPROVED INCENTIVE SPIROMETER

[76] Inventor: Paul Dwork, 1127 Carrido Dr., Camarillo, Calif. 93010

[21] Appl. No.: 375,157

[22] Filed: Jan. 18, 1995

[51] Int. Cl.[6] .................................................. A61M 11/00
[52] U.S. Cl. ................ 128/200.23; 128/725; 128/203.24
[58] Field of Search ......................... 128/203.23, 200.23, 128/200.14, 725, 203.24

[56] References Cited

U.S. PATENT DOCUMENTS

| | | | |
|---|---|---|---|
| 3,695,608 | 10/1972 | Hanson | 128/725 X |
| 4,114,607 | 9/1978 | Russo | 128/725 |
| 4,114,608 | 9/1978 | Russo | 128/725 |
| 4,183,361 | 1/1980 | Russo | 128/725 |
| 4,232,683 | 11/1980 | Bartholomew | 128/725 |
| 4,291,688 | 9/1981 | Kistler | 128/200.23 |
| 4,444,202 | 4/1984 | Rubin et al. | 128/725 |
| 4,484,577 | 11/1984 | Sackner et al. | 128/203.28 |
| 4,576,157 | 3/1986 | Raghuprasad | 128/200.23 |
| 4,790,305 | 12/1988 | Zoltan et al. | 128/200.23 |
| 5,040,527 | 8/1991 | Larson et al. | 128/200.23 |
| 5,431,154 | 7/1995 | Siegel et al. | 128/200.14 |

FOREIGN PATENT DOCUMENTS

| | | | |
|---|---|---|---|
| 3827636 | 2/1989 | Germany | 128/200.23 |
| 84/01704 | 5/1984 | WIPO | 128/725 |

OTHER PUBLICATIONS

Huntley, W. et al., "Evaluation of Bronchodilation from Aerosol B2 Agonists Delivered by the Inhal-Aid Device to Young Children," J. Asthma, 21(4), 1984, pp. 265–270.
Freigang, B., "New Method of Beclomethasone Aerosol Administration to Children under 4 Years of Age," CMA J., vol. 117, Dec. 3, 1977, pp. 1308–1309.
Cutie, A. et al., "Aerosolized Drug Delivery Accessories," Aerosol Age, Mar. 1984, pp. 24 et seq.
Konig, P., "Spacer Devices Used with Metered-Dose Inhalers: Breakthrough or Gimmick?," Chest, 88(2), 1985, pp. 276–284.

*Primary Examiner*—Christopher A. Bennett
*Assistant Examiner*—Eric P. Raciti

[57] ABSTRACT

A unique adaptor and improved incentive spirometer for delivering medication to patients from metered dose inhaler canisters. The improved apparatus is comprised of a unique universal adaptor has an inlet configured to receive a variety of incentive devices, an outlet to connect a mouthpiece and a socket for receiving a metered dose medication canister. The socket is constructed to accept a wide variety of metered dose inhaler spray tips and includes a nozzle spray tip constructed to provide optimum misting. The inlet of the unique, universal adaptor is constructed to receive a variety of incentive devices to improve medication penetration. An improved incentive spirometer for connection to the inlet of the unique universal adaptor is also disclosed. The improved incentive spirometer may also be used for efficient inspiratory and expiratory volume exercising.

17 Claims, 5 Drawing Sheets

METERED DOSE MEDICATION ADAPTOR WITH IMPROVED INCENTIVE SPIROMETER

BACKGROUND OF THE INVENTION

1. Field of the Invention

This invention relates to an adaptor for use with an incentive spirometer and more particularly, relates to an improved incentive spirometer for inspiratory and expiratory volume exercising and a unique adaptor for metering doses of medication.

2. Background Information

Inhalation and respiratory therapists, as well as physicians, have long recognized a need for patient-oriented ways to administer medications through metered does inhalers. A frequent problem is the ability for the patient to inhale the medication and determine the effectiveness of the inhaled treatment. When the patient feels they have not received the proper relief, they will administer more medication and over utilize the medication.

Devices such as spacers have been designed to assist the patient in receiving the proper amount of medication delivered from metered dose inhalers and to improve the capture of medication by the patient. Such devices, including inhaling chambers, help to ensure the patient breaths deeply to penetrate the lungs as much as possible. Such devices have shown some effectiveness with metered dose inhalers, but do not provide the incentive or the ability of a patient to effectively evaluate the efficiency of the treatment. The patient can generally only tell if the treatment is effective, by whether or not that they feel some improvement.

Metered dose medication inhalers are pressurized canisters containing a respiratory medication such as Ventolin or Proventil. The canister usually comes with a dispenser comprised of a tubular housing for receiving the canister, and a spray outlet for engaging the canister spray stem or tip. To dispense a dose of medication, a patient presses the end of the canister into the dispenser housing, which forces the vapor outlet spray tip into the canister, opening a valve and releasing a single dose of medication through a spray nozzle and a mouthpiece on the dispenser. A patient must breath deeply, almost simultaneously, while expelling a dose of medication to allow the medication to reach the lungs. This means that the patient must coordinate the dispensing of the medicine and inhaling simultaneously. It has been estimated that as little 15 percent penetration of the medication is achieved with the conventional dispensing devices.

One such device for dispensing a metered dose medication is shown in U.S. Pat. No. 4,576,157 of Raghuprasad. This patent discloses a dispenser having a housing for receiving a canister of medication such as Ventolin. This patent describes vapor outlet tip being pressed into a stand pipe to spray medication through a nozzle having an air operated sail valve. The problem with this device is the danger of small parts that could accidentally become dislodged and be inhaled.

Various devices have been conceived to improve and simplify the use of the metered dose inhaler dispensers. For example, U.S. Pat. No. 5,042,467 of Foley, describes a medication inhaling chamber or spacer that can be fitted to the mouthpiece of a conventional dispenser. One end of the chamber has a flexible diaphragm to receive the mouthpiece of the conventional dispenser. The other end of the chamber has its own mouthpiece. The patient discharges the metered dose canister through the dispenser into the chamber where it will expand and presumably, more thoroughly vaporize for inhalation through the mouthpiece on the chamber. The construction of the chamber, and inclusion of an audible sonic device is supposed to indicate proper inhalation technique to improve treatment. The sonic device produces a tone if a patient inhales too rapidly. Another device, disclosed in U.S. Pat. No. 5,007,419 of Weinstein et al, is designed to permit the use of multiple metered dose inhaling canisters. This device has a pair of opposing housing or receptacles having a centrally located spray nozzle and mouthpiece. Metered dose inhaler canisters are installed in each end to dispense two different vaporized medications through the spray nozzle and mouthpiece. However, a disadvantage of this device is that it sprays different medications through the same nozzle allowing for potential drug interactions, this practice has been considered unacceptable and has not been approved.

Devices for use with metered dose medication dispensers are also illustrated in U.S. Pat. No. Des. 294,298 of Bush and U.S. Pat. No. Des. 340,975 of Sladek. The former is a design for a bronchial dilator tee while the latter is for an expansion chamber for use with a metered dose medication dispenser. The latter expansion chamber appears to be similar in function and presumably, provides the same benefit disclosed in the United States Patent of Foley referred to hereinabove. There appears to be little difference in function in these two different devices except for their outward appearance.

There are also devices to exercise breathing which permit monitoring control of the volume of inspired air and can indirectly be used to control the rate of inspiration of medications. One such device is disclosed in U.S. Pat. No. 4,444,202. The device disclosed in this patent can be used to indicate the amount of inspired air, but has some problems. The device includes a tube and a valve assembly to calibrate the effective range of the spirometer. A floating ball is used to indicate the effective volume of inspired air. However, because of deficiencies in the design of the breathing exerciser, the ball does not effectively show a controlled rate of inspired air. At some point, the ball will "pop-up" to the top indicating the exerciser is being used at its full range. The design does not permit the ball to rise slowly, accurately indicating the amount of inspired air. Thus, a patient using the device cannot accurately and smoothly control the volume of inspired air.

The breathing exerciser, in the above identified patent, also includes an elongate tube and bulb for using the breathing exerciser as a medication inhaler. Since the breathing exerciser itself does not provide a smooth delivery of inhaled air, its use in conjunction with a medication inhaler is not as effective as it could be.

It would be advantageous if the breathing exerciser of the above identified patent could be improved to provide a smooth and accurate delivery of inspired air. It would also be advantageous if this device could be provided with an adaptor for use with pressurized metered dose medication inhalers.

It is therefore, one object of the present invention to provide an improved incentive inspirator.

Yet another object of the present invention is to provide an improved incentive inspirator and adaptor for use in the administration of medications delivered through a metered dose inhaler.

Yet another object of the present invention is to provide a unique, universal adaptor that provides no free airflow from the point where the nozzle of a metered dose inhaler stem is inserted in the adaptor.

Still another object of the present invention is to provide a universal adaptor providing no free airflow from the point of the nozzle where a metered does inhaler stem is inserted in the adaptor, and provides a second opening that permits attachment of other devices that provide some measurement of the efficiency of the medication inhaled.

Still another object of the present invention is to provide a universal adaptor that provides no free airflow from the point where the nozzle of the metered dose inhaler stem is inserted in the adaptor, and a second opening for attachment of an incentive spirometer.

Yet another object of the present invention is to provide a universal adaptor providing no free airflow from the point where the nozzle of the metered dose inhaler stem is inserted in the adaptor, and includes a second orifice for attachment of a variety of devices such as a whistle for indicating the efficiency of the inhaled medication, another adaptor piggybacked or a cloud chamber attached.

Yet another object of the present invention is to provide a universal adaptor which can provide medication through a closed system where no air is drawn in from the point where the medication is released.

BRIEF DESCRIPTION OF THE INVENTION

The purpose of the present invention is to provide an improved incentive inspirator and universal adaptor for use in administration of medications delivered via metered dose inhalers, or by other aerosolized methods.

The present invention provides improvements to the breathing exerciser, shown and described in U.S. Pat. No. 4,444,202. These improvements include modifications to improve the airflow and reduce the cost of the manufacture and production of the spirometer. The improved airflow also allows an accurate indication of the amount of inspired air by providing accurate control of the ball float in a clear plastic tube to indicate the flow. With the incentive spirometer, adaptor and a mouthpiece attached, a user can accurately control the rate and volume of inspired air and see an indication that the volume of air that is being inhaled.

A problem with the breathing exerciser of U.S. Pat. No. 4,444,202 is that accurate control of airflow is difficult, if not impossible. The airflow indicator is comprised of a ball in a tube resting on a sealing disc, with air inlets opening positioned in the tube slightly below the horizontal center of the ball indicator. While this will allow the ball to rise when the breathing exerciser is used, the ball will not rise smoothly providing an accurate flow control of the volume of air. Often, the ball indicator will "pop-up" from the bottom of the sealing disc to the top indicating a volume of air that equals or exceeds the amount indicated. The improvements proposed will provide a smooth transition of the ball indicator from a rest-position to a floating-position when the incentive inspirator is used.

The improvements in the incentive inspirator are comprised of providing air inlets at the lower or base cap, below the floating ball indicator. A second improvement is the provision of a post that provides a small pedestal for the ball indicator to rest on. These improvements allow a large volume of air to flow beneath, and around the ball indicator providing a smoother transition from a rest-position on the pedestal to the upper end, or maximum volume of the spirometer. With a smooth inhalation of air, the ball will rise gradually and smoothly from the pedestal to any position desired, or all the way to the top.

In addition, molding the inlet tubes at the bottom of the lower or base cap member, eliminated the need for drilling holes in the transparent plastic ball tube which could leave hazardous bits of loose plastic that might be inhaled by the user. In the improved incentive spirometer, vertical holes are molded in the base member that pass around the lateral bore communicating with the circulating air tube.

A further improvement is the inclusion of a universal adaptor for administration of medication via a metered dose inhaler. With the unique adaptor, no air is drawn in from where the medication is released. A conventional mouthpiece can be fitted on the unique, universal adaptor which will provide a means for the patient to expel medication from the metered dose inhaler and breath in the medication. The adaptor also provides a structure that allows the addition of an incentive spirometer such as that shown and described in U.S. Pat. No. 4,444,202 which is preferably modified and improved as disclosed hereinafter.

The addition of an incentive spirometer, of which many types and models are available, provides a way for a patient to accurately and clearly measure their intake. The universal adaptor can also be equipped with a whistle in place of the incentive spirometer, or a variety of additional devices. The adaptor could be equipped or mounted on a y-shaped connector for use with a pair of incentive spirometers or multiple metered inhaler devices. Another alternative is to connect a spiraling dispensing chamber to the adaptor for circulating the medication to improve vaporization before inhalation.

The unique construction of the adaptor also provides for other applications. A variety of constructions for the dispensing jet are available to improve the vaporization of medication and allow different angles of delivery. Variations in delivery angle can be effective in producing a finer mist by impacting vapor on the walls of the tube to reduce particle size. New medications under development can benefit from this ability to vary and improve particle size. Additionally, the adaptor can be cascaded for use with multiple metered dose inhalers. The adaptor of the present invention permits a wide range and variety of uses for metered dose inhalers. None of the United States patents disclosed and discussed above, provide the versatility or any use that is similar.

The above and other novel features of the invention will be more fully understood from the following detailed description and the accompanying drawings, in which:

DETAILED DESCRIPTION OF THE INVENTION

Figures 1, 1A, 4, 5:
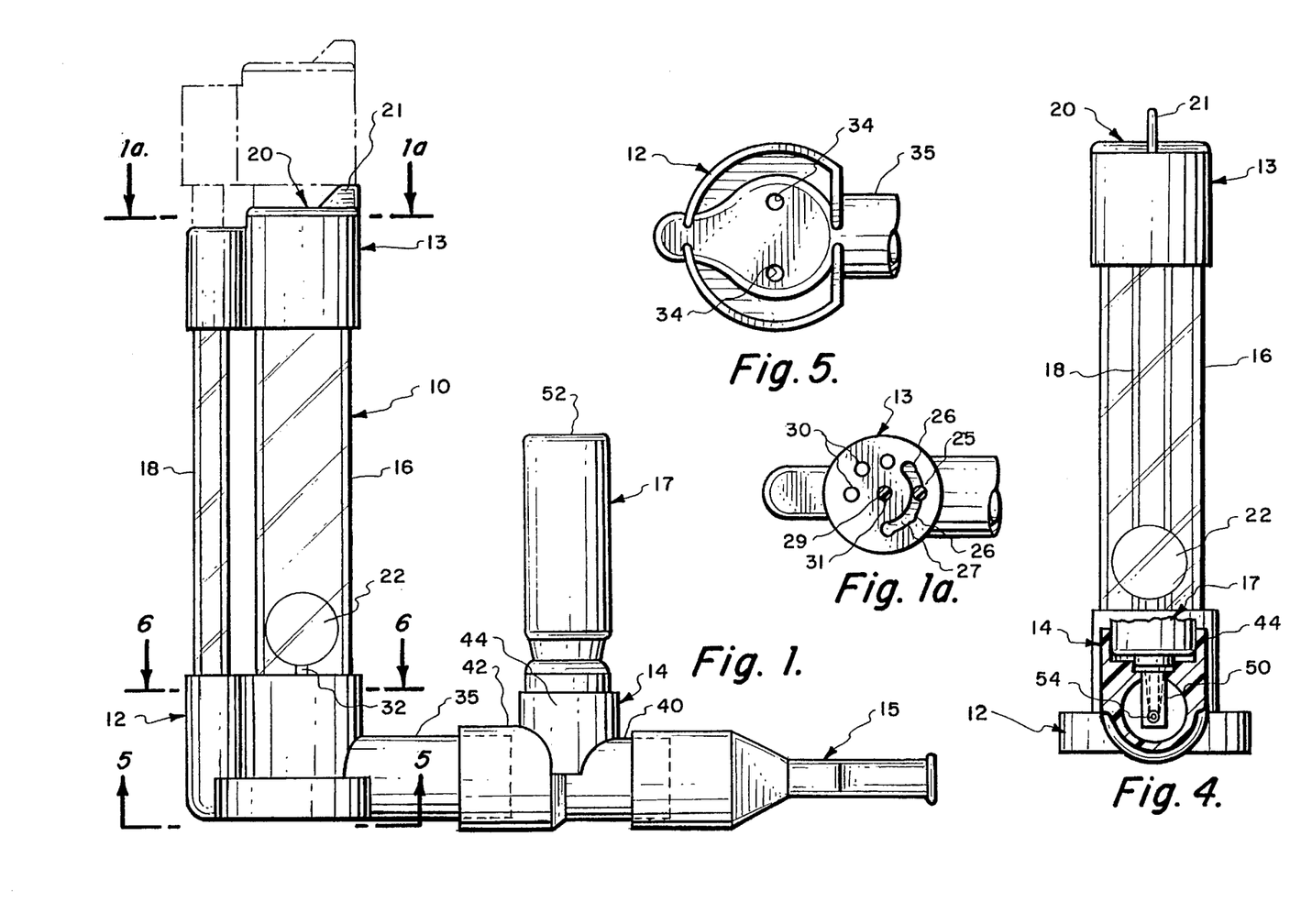
FIG. 1 is a side elevation of an incentive spirometer attached to the unique, universal adaptor according to the invention.
FIG. 1a is a sectional view taken at 1a—1a of FIG. 1.
FIG. 4 is a sectional view taken at 4—4 of FIG. 3.
FIG. 5 is a view taken at 5—5 of FIG. 1.

A unique system for use with metered dose inhaling canisters is illustrated in FIG. 1. The apparatus of FIG. 1 is comprised of an incentive spirometer 10 connected to a mouthpiece 15 by a unique, universal adaptor 14 for mounting a metered dose medication inhaler 17. Universal adaptor 14 can be used with wide variety of devices as will be described in greater detail hereinafter.

Incentive spirometer 10 is an improved version of the breathing exerciser disclosed and described in U.S. Pat. No. 4,444,202 described above, and incorporated herein by reference. Incentive spirometer 10 is comprised of a base cap 12, a top cap 13, an indicator tube 16 and a circulating tube 18. Maximum flow is controlled by a valve 20 mounted on top of top cap 13 as disclosed and described in the United States patent referred to hereinabove. Incentive spirometer 10 has been improved to provide more accurate placement of the directional airflow and smoother operation.

Indicating ball 22 is provided in transparent indicating tube 16 rises and falls according to the flow volume. The position of the ball in the tube indicates the flow of air through the inspirator in cubic centimeters (cc) by a scale (not shown) that may be printed on indicator tube 16. With the improved construction, that will be described hereinafter, a patient breathing through mouthpiece 15 can accurately control the movement of indicator ball 22 in indicator tube 16 and visually observe the flow of volume on a scale (not shown) provided on the indicator tube 16. Unique and improving modifications of the breathing exerciser provide a greater flow of air around indicator ball 22 allowing it to be easily and accurately raised in indicator tube 16. With a spirometer constructed, as disclosed in the above identified patent, indicator ball 22 does not rise smoothly, and may not move at all until the volume of air reaches a maximum when the ball will then jump to the top of indicator tube 16. Thus, the patient could not effectively maintain accurate control of the volume.

With the modifications disclosed herein, a patient can effectively and smoothly control the volume from the minimum with the ball only slightly raised at the bottom of indicator tube 16, to the maximum where the ball is at the top of the indicator tube. A unique advantage of the improved construction also allows a heavier ball to be used for increasing the flow volume.

Flow volume adjustment valve 20 allows maximum volume selections of 750 cc's (cubic centimeters) to 3,000 cc's in 750 cc increments. With flow valve 20 completely closed, the flow volume will register a maximum at only 750 cc's. That is, volume flow control valve 20 is completely closed, an inhalation rate that moves indicator ball 22 to the top of indicator top 16, will indicate a flow volume of 750 cc's/second. Each adjustment of flow volume control valve 20 indicates an increase of 750 cc's in the maximum volume measured. Thus, the second position will indicate a maximum 1,500 cc flow with indicator ball 22 at the top of indicator tube 16. These flow volumes can be further adjusted by increasing the weight of ball 22. With the device of the prior patent, increasing the weight of ball 22 could prevent the device from operating because of the low volume of air lifting the ball.

Figures 2, 3, 6:
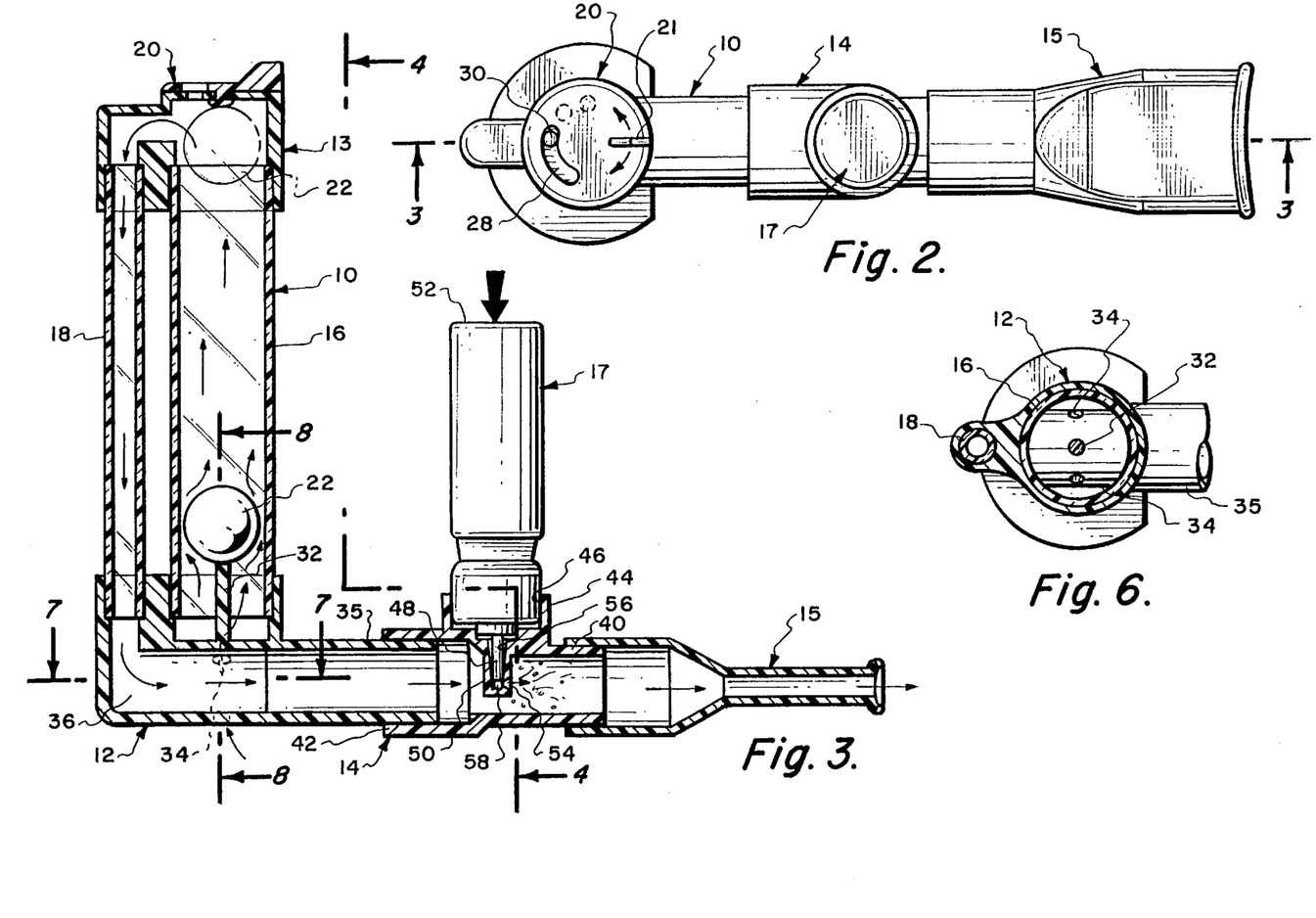
FIG. 2 is a top view of the incentive spirometer andunique, universal adaptor illustrated in FIG. 1.
FIG. 3 is a sectional view taken at 3—3 of FIG. 2.
FIG. 6 is a sectional view taken at 6—6 of FIG. 1.

The construction of flow volume control valve 20 is improved as shown in FIGS. 1a and 2. Top cap 13 is provided with a series of holes 30 that are in selective registration with arcuate slot 28 provided in rotatable disc 24. The position of arcuate slot 28 is selected by rotation of disc 24 with knob 21 from side to side as indicated by the arrows. Disc is rotatably mounted on top of top cap 13 by a shaft 29 seated in hole 31. Selective position of disc 24 is provided by pin 25 on the underside of disc 24 engaging detents 26 in arcuate groove in top cap 13. This unique construction provides a positive feedback of the selected position which can be both felt and heard. A clearly audible click can be heard and felt as pin 25 on rotatable disk 24 moves from one detent 26 to another as disc is rotated by knob 21. The more holes 30 exposed by adjustment of slot 28 in disc 24 the greater the flow of air.

The operation of flow volume control valve 20 is shown more clearly in FIG. 2. Knob 21 allows disc 24, secured to top cap 13, to increase or decrease the amount of air that can flow through the valve by the position of slot 28 relative to holes 30. This flow offsets the flow for lifting indicator ball 22. Pin 25 engages detents 26 that hold valve slot 28 in a selected position. With knob 21 in the position shown, slot 28 in disc 24 exposes one hole 30 in the top cap 31 allowing air to flow into incentive spirometer 10. This means a larger volume of air must be inhaled by the patient to move ball indicator 22 to the top of indicator tube 16. Further adjustment, in a clockwise direction, increases the amount of air that can enter through valve 20 indicating an increase in the volume of air inhaled.

Incentive spirometer 10 has been improved to allow more accurate control of indicator ball 22 by a patient. A pedestal 32 is formed by a post on the bottom of base cap 12 to hold indicator ball 22. Pedestal 32 provides a support that is very small in diameter compared to indicator ball 22 allowing more air to flow around the ball as indicated by ball 22, and as indicated by the arrows to provide a smoother lift-off. Since more air can be used to lift ball 22, the position of the ball can be more effectively controlled. The height of pedestal 32 can be changed in manufacture to provide a change in the volume range of air measured by the incentive spirometer.

Figure 7:
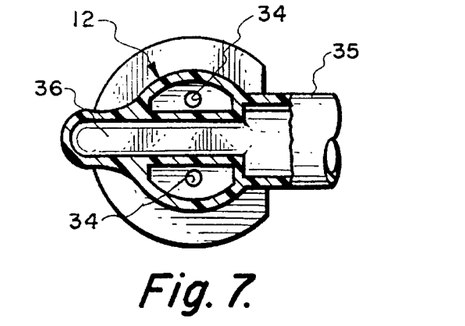
FIG. 7 is a sectional view taken at 7—7 of FIG. 3.
Figure 8:
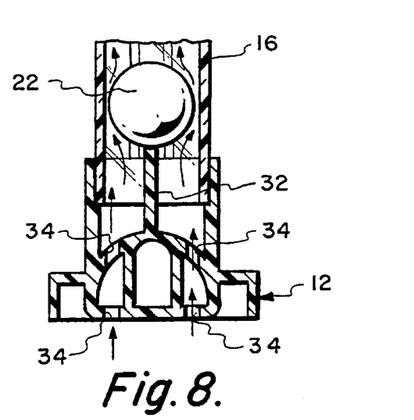
FIG. 8 is a sectional view taken at 8—8 of FIG. 3.

Another improvement is in the passageways for air to enter indicator tube 16. These passageways are shown more clearly in FIGS. 6 through 8. A pair of passages 34 are provided in the base of bottom cap 12, on opposite sides of passageway 36, in communication with indicating tube 16. This means that air flowing into incentive spirometer 10 comes from directly below indicator ball 22 into indicator tube 16. This provides a larger airflow around indicator ball 22 because of the small pedestal 32 supporting ball above the bottom of indicator tube 16. Inlet 35, in bottom cap 12, connects adaptor 14 and mouthpiece 15 to bottom cap 12.

The improved construction of the incentive spirometer allows its effective use with a metered dose medication canister 17 through unique, universal adaptor 14. Universal adaptor 14 is used to deliver metered dose medications. Adaptor 14 is designed to be used with all types of metered dose inhalers, and can therefore, be considered a universal adaptor. The concept of different directional spray patterns takes into account different types of medications to be delivered. Powders impacting the side wall of the adaptor prior to being inhaled for example. T-shaped Adaptor 14 has outlet 40 constructed to receive mouthpiece 15. Inlet end 42 is designed to receive incentive spirometer 10, or some other incentive device to provide resistance when a patient is inhaling medication from metered dose inhaler canister 17. Adaptor 14 has socket 44 having a universal opening 46, constructed to accept a wide range of all metered dose inhaler canister tips. This eliminates the need for a patient to carry a separate dispensing unit for delivery of different medications used. Presently, all metered dose inhaler canisters are supplied by the manufacture with a handheld dispensing unit to supply the medication. Each of these dispensing units are specific to the manufacturer, and no other medication canisters will ordinarily operate with that manufacturer's unit.

Adaptor 14, by having an opening on each end at outlet 40 and inlet 42, can couple to a mouthpiece at one end and at the same time, attach to incentive devices such as incentive spirometer 10. The unique aspect of the adaptor is that it can accommodate both the metered dose inhaler canister 17 and be connected to mouthpiece 15 at one end and to an incentive device at inlet end 42, such as incentive spirometer 10.

When universal adaptor 14 is connected to mouthpiece 15 at outlet end 40, and incentive spirometer 10 at inlet 42, the apparatus can define a much more effective treatment device than prior metered dose inhaler dispensers. Metered dose inhaler canister 17 is seated in socket 44 with spray tip 48 seated in spray nozzle 50. Downward pressure on end 52 of metered dose medication canister 17, forces spray tip 48 into the canister opening a valve and ejecting a dose through jet 54 in spray nozzle 50 of adaptor 14. Simultaneously, while ejecting a dose of medication from canister 17, a patient will breath deeply through mouthpiece 15 and incentive spirometer 10. The patient can clearly see the volume of air flowing through incentive spirometer 10 as the medication is 16 being inhaled. With canister 17 seated in socket 44 of adaptor 14 and incentive spirometer 10 connected to inlet 42, no air is drawn in from the opening where metered dose inhaler canister 17 is seated. This unique construction of adaptor 14, for receiving incentive spirometer 10 and mouthpiece 15, has never been provided before. This allows a patient to inhale medication from metered dose inhaler canister 17 with resistance applied by incentive spirometer 10 resulting in the benefit of medication penetrating deeper into the lungs.

A patient can now, not only deliver an effective metered dose of medication, but can effectively control the volume of air inhaled by observing incentive spirometer 10.

Universal adaptor 14 is shown in greater detail with the various modifications and for use with various devices in FIGS. 9 through 13. Adaptor 14 has outlet end 40 for receiving a mouthpiece 15, receptacle 44 for receiving a metered dose canister 17 and inlet 42 for receiving a variety of inhaling incentive devices to provide resistance when a patient is inhaling medication from metered dose canister 17. Nozzle 50 has a passageway 56 for receiving spray tip 48 on metered dose canister 17. Passageway 56 tapers slightly from nozzle jet 54 outward to accommodate and accept a variation of spray tip sizes from various metered dose inhalers currently available. A shoulder 58, in passage way 56 abuts the end of spray tip 48. Shoulder 58 forces spray tip upward when a downward force is applied to end 52 of canister 17 as shown in FIG. 3 by the arrow. This downward force causes spray tip 48 to open a valve in metered dose canister 17, ejecting a dose of medication through nozzle jet 54.

Figure 9:
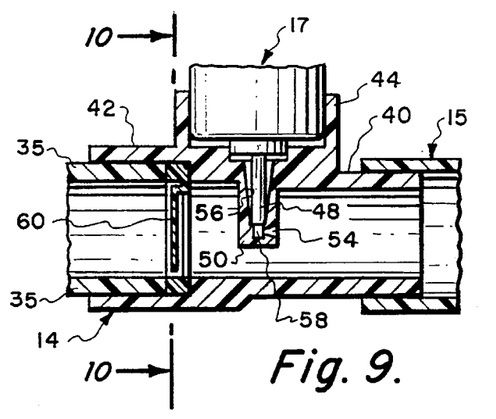
FIG. 9 is a partial section illustrating another application for the unique, universal adaptor.
Figure 10:
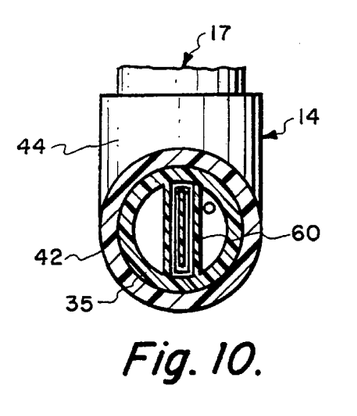
FIG. 10 is a sectional view taken at 10—10 of FIG. 9.

Adaptor 14 is also constructed to accept a wide variety of incentive devices to provide resistance to improve medication penetration. In FIGS. 9 and 10, a whistle 60 has been inserted in inlet end 42 of adaptor 14 to provide a resistance during use of the metered dose inhaling adaptor. Whistle 60 will provide an audible tone indicating when the patient has achieved optimum inhalation volume to get the most medicine penetration to the lungs.

Figure 11:
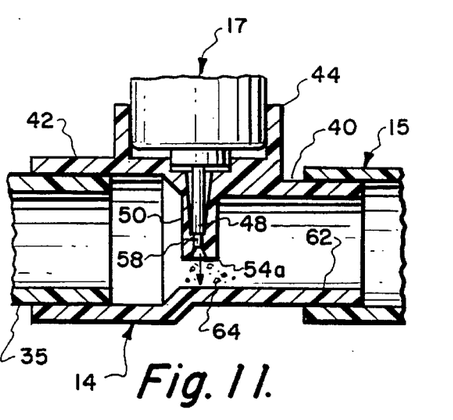
FIG. 11 is a partial sectional view of the unique, universal adaptor having a modified spray pattern illustrating that the angular direction of the jet orifice can be changed for different models of adaptors.

In one aspect of the invention, nozzle jet 54 can be modified to improve misting of the medication sprayed from metered dose canister 17. It is important that the droplets of medicine expelled from canister 17 be in as fine a mist as possible. The modifications shown in FIGS. 11, 12 and 13 can aid in breaking up the droplets to deliver the medicine in a finer mist. In FIG. 11, nozzle 50 includes a nozzle jet 54a pointing directly down at interior wall 62 of adaptor 14. As medicine, indicated by droplets 64, is ejected from jet 54a it impinges on wall 62 and will break the spray up into a finer mist.

Figure 12:
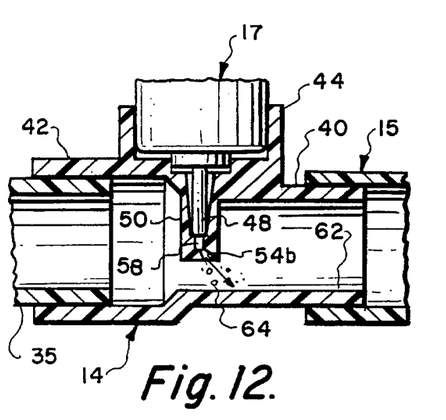
FIG. 12 is another partial section of the unique, universal adaptor with a further modification of the spray pattern.

Another embodiment is illustrated in FIG. 12 in which nozzle 50 has a spray jet 54b that is angled slightly toward outlet end 40. Again, the droplets of spray 64 impinge on wall 62 of adaptor 14 creating a finer mist.

Figure 13:
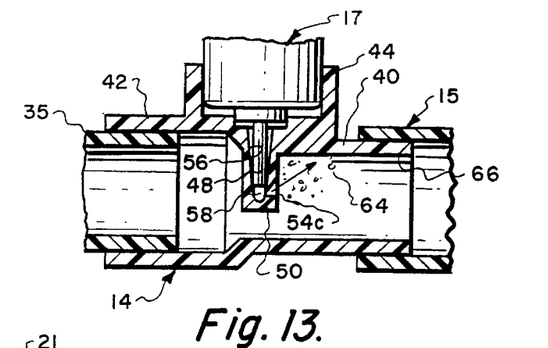
FIG. 13 is yet another partial section of the unique, universal adaptor having another modification of the spray pattern.

A third modification is illustrated in FIG. 13 in which spray nozzle 50 has a spray jet 54c angled upward to cause medication 64 to bounce off upper wall 66 to create and improve the mist. The exit not only can improve the mist, but in some cases the impact of the medication on the wall can break-up the particle size.

Figure 14:
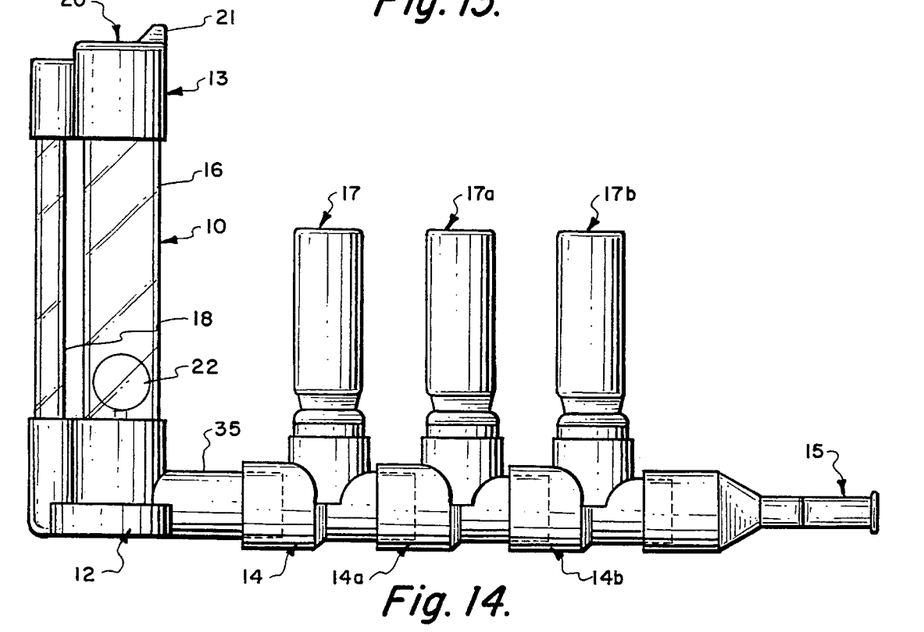
FIG. 14 is a side elevation illustrating a cascade connection of multiple adaptors with multiple metered dose medication canisters connected to an incentive spirometer on one end, and a mouthpiece at the other.

The versatility of unique adaptor 14 is illustrated in FIGS. 14 through 18. The embodiment illustrated in FIG. 14 shows the system being used with multiple metered dose canisters 17, 17a and 17b. The unique construction of adaptor 14 allows multiple adaptors to be cascaded in series as shown by adaptors 14, 14a and 14b connected between mouthpiece 15 and incentive spirometer 10. This configuration is unique and avoids disadvantage and the unacceptable practice of spraying multiple metered dose medications from a single spray tip as shown in U.S. Pat. No. 5,007,419. In this embodiment, each spray tip and nozzle will be separate allowing selective spray of any of the medications from metered dose canisters 17, 17a and 17b.

Figure 15:
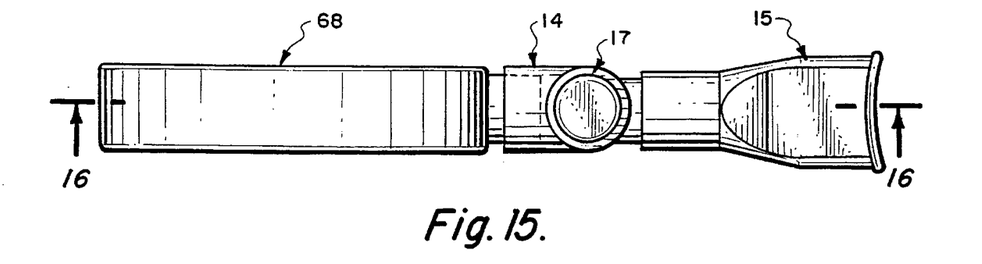
FIG. 15 is top view of the unique, universal adaptor connected to a spiraling dispensing chamber or aerosol cloud chamber.
Figure 16:
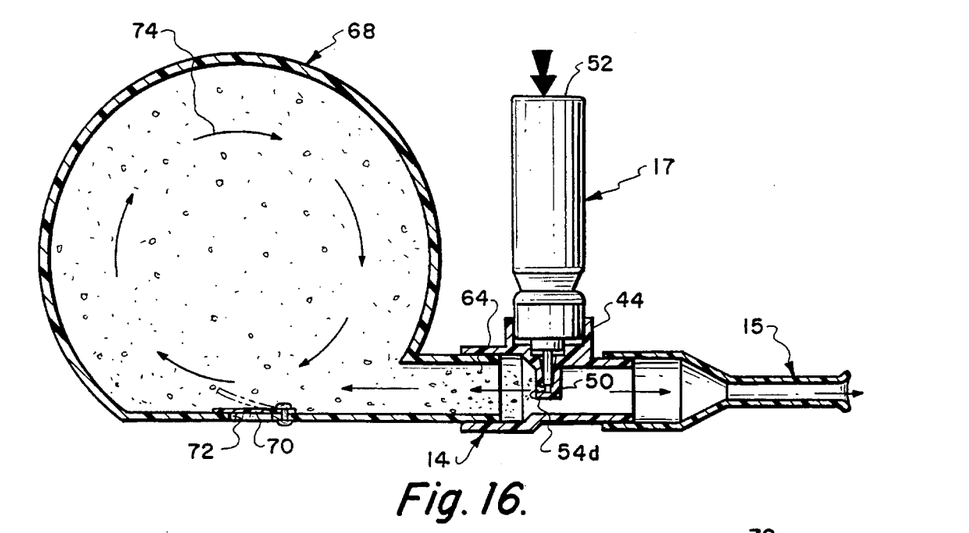
FIG. 16 is a sectional view taken at 16—16 of FIG. 15.

Adaptor 14 may also be used with other incentive devices such as a spiraling mist cloud chamber 68 as shown in FIGS. 15 and 16. Spiraling mist cloud chamber 68 has a disc valve 70 and an inlet 72 to allow air to be drawn in to circulate medication 74 expelled from canister 17 into spiraling mister 68. In this embodiment, adaptor 14 has a nozzle 50 with a jet 54d facing toward spiraling mist chamber 68. A downward force on end 52 of canister 17, as indicated by the arrow, causes a dose of medication 64 to be ejected into spiraling mist cloud chamber 68. As the patient inhales through mouthpiece 15, air enters through hole 72 and valve 70 causing the medication to spiral around the chamber breaking up the droplets and improving vaporization of medication into a finer mist allowing the patient to deeply breath in the medication.

Figures 17, 18:
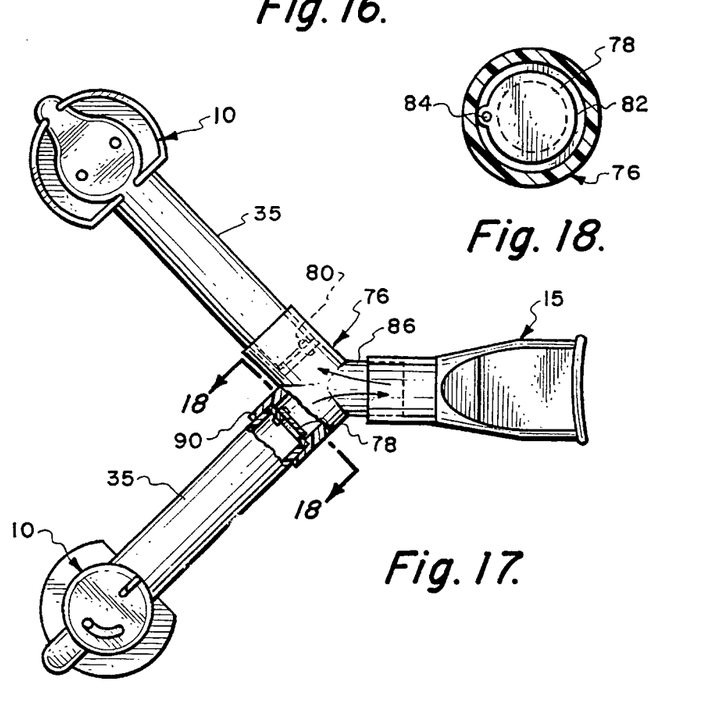
FIG. 17 illustrates the unique joining of two incentive spirometers through a y-shaped connector to a single mouthpiece allowing for inspiratory and expiratory exercise simultaneously.
FIG. 18 is a sectional view taken at 18—18 of FIG. 17.

Another application of the adaptor is illustrated in FIGS. 17 and 18. In this embodiment, adaptor 14 can be used with multiple incentive spirometers 10 can be used by connecting them through a y-shaped connector 76. Each y-shaped connector has a disc-type check valve 78 and 80 to control the flow of air. A typical disc valve is shown in FIG. 18 and is comprised of a flange 82 inside y-shaped connector 76 and a flexible disc 78 secured by a pin 84. Y-shaped connector 76 has a inlet/outlet connecting end 86 for connecting mouthpiece 15. The opposite end splits into an outlet end 88 going to an incentive spirometer 10 that is oriented upside down to measure expelled air. The other end of y-shaped connector 76 is an inlet 90 for air flowing from a second incentive spirometer 10 for measuring the volume of air inhaled. Thus, the device shown can measure the volume of air inhaled as well as the amount of air exhaled.

This embodiment allows the improved incentive spirometer to be used for continuous inspiration and expiration exercising.

Thus, there has been disclosed an improved incentive spirometer and a unique, universal adaptor that can be used for a wide variety of applications. The incentive spirometer has an improved airflow as well as improvements to provide a smoother control of airflow. The post forming the pedestal for mounting the ball can be varied in height and the weight of the ball can be varied to provide a wide range of air volume indications. The unique, universal adaptor can be used with a variety of incentive devices to provide resistance when inhaling a metered dose medication. It can be used with a whistle to indicate when optimum inhaling pressure is applied or can be cascaded to deliver multiple medications. The unique, universal adaptor can also be used with a variety of chambers as well as used with multiple incentive spirometers by connecting to a y-shaped adaptor for providing an inhaling/exhaling exerciser.

This invention is not to be limited by the embodiment shown in the drawings and described in the description which is given by way of example and not of limitation, but only in accordance with the scope of the appended claims.

What is claimed is:

1. An inspiratory flow control device for controlling inspiratory airflow under resistance for inhalation therapy comprising:
    a first universal adaptor having means for receiving an MDI canister having a spray tip, said first universal adaptor having a first end and a second end and an axis connecting said ends;
    a tapered mouthpiece connectable to said first end of said first universal adaptor, said tapered mouthpiece providing means for accelerating a flow of air passing through said first universal adaptor and into the mouth of a user;
    an incentive spirometer means connectable to said second end of said first universal adaptor, said incentive spirometer means for indicating a user's inhalation flow rate and for indicating the optimal inhaled volume for activation of an MDI canister; said incentive spirometer further comprising selectably variable resistance means for regulating inspiratory airflow.

2. The inspiratory flow control device of claim 1 wherein said first universal adapter further comprises a whistle.

3. The inspiratory flow control device of claim 1 wherein said first universal adaptor further comprises a tapered passageway means for accepting a variety of MDI canister nozzles.

4. The inspiratory flow control device of claim 1 wherein said first universal adaptor further comprises a nozzle jet.

5. The inspiratory flow control device of claim 4, wherein said nozzle jet is angled with respect to said axis of said first universal adaptor.

6. The inspiratory flow control device of claim 1 further comprising a second universal adaptor and receiving a second MDI canister and spray stem, and having a first end and a second end; said second end of said second universal adaptor connectable to said first end of said first universal adaptor, and said first end of said second universal adaptor connectable to said mouthpiece.

7. The inspiratory flow control device of claim 30, wherein one or more additional universal adaptors are selectably connectable in end-to-end fashion between said first and second universal adaptors.

8. The inspiratory flow control device according to claim 1 in which said incentive spirometer comprises; first and second tubes; a bottom cap constructed to receive a lower end of said first and second tubes; a top cap constructed to receive and connect an upper end of said first and second tubes; a regulating ball in said first tube; a cylindrical pedestal in said bottom cap to hold said regulating ball spaced from the bottom end of said first tube, the diameter of said pedestal being substantially smaller than the diameter of said first tube; an outlet in said bottom cap communicating with said second tube for connecting a mouthpiece; air inlet means in the bottom cap in communication with said first tube; whereby air drawn through said outlet causes air to be drawn through said inlet in said first tube to raise said ball in said first tube so that said ball indicates the volume of air being inspired.

9. The inspiratory flow control device according to claim 8 further comprising selectably variable resistance means having a plurality of holes in said top cap; a rotatable disc mounted on said top cap; said rotatable disc having an arcuate slot for selective registration with said plurality of holes; whereby rotation of said disc increases or decreases the maximum volume of airflow in said incentive spirometer.

10. The inspiratory flow control device according to claim 9 in which said selectably variable resistance means includes incremental means for varying airflow volume in selected incremental amounts.

11. The apparatus according to claim 10 in which said incremental means comprises; an arcuate channel in said top cap; a plurality of spaced apart detents in said arcuate channel; and a pin on said rotatable disc engaging said arcuate channel; whereby rotation of said rotatable disc moves said pin from one detent to another to provide a positive indication of an incremental adjustment in airflow volume.

12. The inspiratory flow control device according to claim 1 in which said selectably variable resistance means comprises; a plurality of hole in said top cap; a rotatable disc mounted on said top cap; said rotatable disc having an arcuate slot for selective registration with said plurality of holes; whereby rotation of said disc increases or decreases the maximum volume of airflow in said incentive spirometer.

13. The inspiratory flow control device according to claim 12 in which said valve means includes incremental means for varying airflow volume in selected incremental amounts.

14. The inspiratory flow control device according to claim 13 in which said incremental means comprises; an arcuate channel in said top cap; a plurality of spaced apart detents in said arcuate channel; and a pin on said rotatable disc engaging said arcuate channel; whereby rotation of said rotatable disc moves said pin from one detent to another to provide a positive indication of an incremental adjustment in airflow volume.

15. An improved inspiratory and expiratory breathing exerciser comprising:

a pair of incentive spirometers, each said incentive spirometer comprising first and second tubes; a bottom cap constructed to receive a lower end of said first and second tubes; a top cap constructed to receive and connect an upper end of said first and second tubes; a regulating ball in said first tube; an outlet in said bottom cap communicated with said second tube for connecting a respiratory flow; air inlets in the bottom cap in communication with said first tube; and selectably variable resistance means for regulating respiratory airflow; whereby air drawn through said outlet causes air passed through said inlet in said first tube to move said ball in said first tue so that said ball indicates the volume of air passing through the spirometer;

a first of said pair of incentive spirometers being oriented right side up, a second of said pair of incentive spirometers being oriented upside down;

a y-shaped adaptor having an inlet/outlet for connecting a mouthpiece; an inlet connected to said first incentive spirometer and an outlet connected to said second incentive spirometer;

whereby said breathing exerciser meters inhaled and exhaled air when said outlets in said bottom caps of said incentive spirometers are subject to respiratory flow through said y-shaped adaptor.

16. The improved breathing exerciser of claim 15 wherein each of said selectably variable resistance means further comprises: a plurality of holes in said top cap; a rotatable disc mounted on said top cap; said rotatable disc having an arcuate slot for selective registration with said plurality of holes; whereby rotation of said disc increases or decreases the maximum airflow in said incentive spirometers.

17. The improved breathing exerciser of claim 16 wherein each of said selectably variable resistance means further comprises a pin on said rotatable disc engaging said arcuate slot.

* * * * *